(12) United States Patent
Abecassis

(10) Patent No.: US 7,595,061 B1
(45) Date of Patent: Sep. 29, 2009

(54) METHOD FOR USING AN INDUCED FORMATION OF CHITINASE IN LAWN AND GARDEN SOIL FOR THE CONTROL OF DESTRUCTIVE INSECTS AND MICROORGANISMS THEREIN

(76) Inventor: David Abecassis, 64 Manchester Rd., Huntington, NY (US) 11743

( * ) Notice: Subject to any disclaimer, the term of this patent is extended or adjusted under 35 U.S.C. 154(b) by 877 days.

(21) Appl. No.: 11/028,984

(22) Filed: Dec. 13, 2004

Related U.S. Application Data

(63) Continuation-in-part of application No. 10/189,304, filed on Jul. 3, 2002, now abandoned.

(51) Int. Cl.
*A01N 25/32* (2006.01)
(52) U.S. Cl. ............... 424/406; 424/93.4; 424/405; 424/538; 424/547; 435/170; 435/254.1; 514/55; 536/20
(58) Field of Classification Search .......... 424/405
See application file for complete search history.

(56) References Cited

U.S. PATENT DOCUMENTS 4,751,081 A * 6/1988 Suslow et al. ............ 424/93.2
5,811,095 A * 9/1998 Williamson et al. ........ 424/94.2

* cited by examiner

*Primary Examiner*—Neil Levy
(74) *Attorney, Agent, or Firm*—Edwin D. Schindler

(57) ABSTRACT

A method for controlling the growth of destructive insects and microorganisms in ground soil, includes the step of adding chitin to ground soil for inducing bacteria in the ground soil to synthesize chitinase for controlling the spread of destructive insects and microorganisms therein. The chitin may be added to the ground soil by distributing it on the upper surface of the soil or, preferably, by incorporating into the soil. In a preferred embodiment, the step of deacetylating the carbohydrate chains of the chitin for is carried out before adding to the ground soil for increasing the aqueous solubility of the chitin by producing smaller polymeric units or by increasing the availability of polar hydroxyl groups on glucosyl moieties thereof. Various bacterial cultures may also be added to the chitin prior to its distribution on, or incorporation in, the ground soil. A method for using dried shrimp shells for the production of an economically-viable non-genetically-modified organism-based chitinase lawn and garden fermentation broth, for eventual addition to ground soil for controlling the growth of destructive insects and microorganisms in ground soil, is also provided.

13 Claims, No Drawings

METHOD FOR USING AN INDUCED FORMATION OF CHITINASE IN LAWN AND GARDEN SOIL FOR THE CONTROL OF DESTRUCTIVE INSECTS AND MICROORGANISMS THEREIN

CROSS-REFERENCE TO RELATED APPLICATION

This is a continuation-in-part of application Ser. No. 10/189,304, filed Jul. 3, 2002, now abandoned; the entire disclosure of which shall be deemed to be incorporated by reference herein.

BACKGROUND OF THE INVENTION

1. Technical Field of the Invention

The present invention relates, generally, a method for controlling pathogens in lawn and garden soils using an induced formation of chitinase.

More particularly, the present invention provides a method for inducing formation of chitinase enzyme in soil to degrade the chitin present in fungi and insects, e.g., nematodes, and to minimize their destructive effect on lawn and garden vegetation.

Chitinase enzymes can be readily produced by aerobic fermentation in the presence of soil microbes, which produce enzymes and biodegradation products, which, in turn, can be used as a bio-pesticide/fertilizer.

2. Description of the Prior Art

Soil contains a diversity of life forms which can interact with plants, such life forms including bacteria, fungi and nematodes. These biological forms are particularly abundant in the rhizosphere, the area of soil that surrounds and is influenced by the plant roots. Rhizobacteria are those bacteria which are adapted to the rhizosphere. There is a complex interaction among the various life forms in the soil, where some are antagonistic and others are mutually beneficial. Similarly complex is the interaction between the plants and the soil life forms, which can helpful to the plant in some instances, and harmful in others. Nematode pathogens harmful to plants include species from the genera *Meloidogyne, Heterodera, Ditylenchus,* and *Pratylenchus*. Nematode-caused plant diseases include root galls, root rot, lesions, "stubby root," stunting, as well as other rots and wilts resulting from pathogenic fungi effects on nematode-weakened plants. Fungal species that are harmful to plants come from a wide variety of genera, including *Fusarium, Pythium, Phytophthora, Verticillium, Rhizoctonia, Macrophomina, Thielaviopsis* and *Scierotinas*. Plant diseases caused by fungi include pre- and post-emergence seedling damping-off, hypocotyl rots, root rots, crown rots and vascular wilts.

The exoskeleton structure of insects is characterized by the presence of chitin, which is also an essential element in the hyphae of fungi, including the Ascomycetes, Basidiomycetes and Zygomycetes. Chitin is a nitrogen-containing biopolymer, a polysaccharide, consisting of unbranched chains of -(1,4)-acetamide-2-deoxy-D-glucose, also termed poly(N-acetyl-D-glucosamine.) Chitin is found in fungi and arthropods, where it is a principal component in the exoskeletons. In nematodes it not only covers the adult form, but the eggs and cysts as well. Chitin may be regarded as a derivative of cellulose, the main structural support of trees and plants, in which the C-2 hydroxyl groups have been replaced by acetamide residues. The term chitinase refers to the various forms of the family of hydrolytic enzymes that catalyze the depolymerization of chitin by endolytic and exolytic mechanisms.

The endochitinases, represented by many chitinases in plants, cleave the internal -1,4-glycosidic linkages of chitin to produce oligomers of at least three monomeric units. The exo-chitinases, such as the bacterial chitinases elaborated by *Serratia marcescens,* hydrolyze terminal monomer linkages. In addition, chitin can be deacetylated to chitosan with chitin deacetylase. That leaves a polymer chain with an amino group on each glucose linkage.

The major source of chitin, however, is marine fauna, generally as a by-product of the seafood industry. These include crab, lobster and shrimp shells. As a raw material, chitin is, therefore, plentifully available and practically free. Huge amounts of chitin are thrown away each year as a waste material. Purified chitin is relatively expensive to obtain, however, since seafood shells are tough composite materials, and by their very nature resistant to chemical attack. Thus, a vigorous extraction procedure must be applied to obtain the pure material.

Chitin is synthesized extensively by insects at the end of their larval stage and at transitions in their various life cycles, such as wing and new exoskeleton formation after shedding. Because chitinase degrades chitin, it thereby acts as a biocide for insect and fungal pathogens. The degradation of chitin makes insects more vulnerable to various toxicants, microorganisms and parasites which can penetrate the chitin-reduced exoskeleton. Environmental chitinase can also interfere with life cycle changes in insects, such as pupae formation.

To take advantage of this degradative activity, natural evolutionary processes have led to the development of genetic structures in certain plants, plant seeds and fungi which code for the production of chitinase. For example, chitinase has been shown to be induced in rhizoctonia solani-infected rice plants. Also, a number of fungi which are pathogenic to insects have been demonstrated to produce and use chitinase as part of their invasion of their insect hosts.

Harman et al., U.S. Pat. No. 5,173,419, has isolated and characterized the chitinases from trichoderma harzianum which inhibit the activity of chitin-containing fungi and insects. These chitinases can be applied to plants, or to the surrounding soil, in order to protect them. Harman et al. suggests that the genes coding for the chitinases can be isolated and, for example, inserted into the genome of a microorganism to provide a transgenic microorganism capable of producing chitinase as a biocontrol agent.

In bacteria, an induced chitinase enzyme level has been demonstrated in a specific strain of *Serratia*, where higher chitinase yields were produced by the strain when chitin was present in the medium. Suslow et al. have disclosed novel bacterial strains and/or plants which are created by the introduction of foreign DNA linked to a sequence encoding for the production of chitinase, for the purpose of inhibiting plant pathogens. See, U.S. Pat. Nos. 4,751,081; 4,940,840; 5,290,687; 5,374,540; 5,554,521; 5,633,450; and, 5,776,448.

For example, genetically-modified wheat has demonstrated the ability to prevent fungal infection by reducing the attachment of spores and their ability to invade. As a specific example of bacterial biocontrol of a fungal patho-pathogen, it has been demonstrated in the prior art (Kobayashi and El-Barrad 1996) that a newly-classified bacterium, *Lytobacter kobii,* is capable of controlling summer patch disease of Kentucky bluegrass through the production of a number of extracellular lytic enzymes, including chitinase and -1-3-glucanase. These directly damage fungal tissue and are believed to contribute to the organism's ability to parasitize the turf pathogen (M. Poae.)

It has also been reported in the art that pregnant thoroughbred mares in Kentucky have been losing hundreds of their foals as a result of an illness that scientists believe to be a result of a fungus growing on the State's famous bluegrass. The patch-disease fungus is known to produce a number of toxins which are lethal to grazing animals, such as horses and cattle.

The adaptation of soil bacteria to produce chitinase from chitin can be inferred from a study in 1982, conducted Auburn University's Agricultural Experiment Station, which showed that the addition of chitin to soil had an inhibitory, or direct, biocidal effect on soil nematodes. Biodegradation of the chitin is believed to result in high soil ammonia, which is toxic to many nematode species. But the soil bacteria also elaborated chitinase, which attacks the protective, chitinous outer layer of nematode eggs. That same study also revealed that chitin added to soil at loading rates of 2% inhibited seed germination in a number of plants, which effect has been ascribed to the inhibition of necessary fungal degradation of the outer seed coating. It is also possible that excess ammonia or nitrate levels produced by the degradation of nitrogenous chitin was causing phytotoxicity.

An attempt to harness the induced production of chitinase by a growing plant was provided recently by Stoner et al., U.S. Pat. No. 6,193,988, which disclosed a disease-controlling planting system comprising a plurality of parts. A typical system disclosed by Stoner et al. would include a propagule (e.g. a potato eye), chitin and chitosan (deacylated chitin)—to trigger the release of a naturally defensive substance from the propagule to protect itself from disease, a non-gaseous communication medium, and an encapsulant, in which the propagule can develop until it is able to withstand disease on its own. The natural defensive systems said to be released would include chitinase, beta-1,3-glucanase, protease inhibitors, phenylalanine lyase, chitosanase, and PR1-5 proteins.

Homeowners and other people concerned with maintaining home gardens and lawns, as well as turf such as golf courses to which the general public can be exposed, are continuously and increasingly concerned about the use of chemical pesticides and fertilizers for their proper control. And, for produce grown in these gardens, consumers have expressed a desire for organically-based pest control agents. In addition, the use of chemical pesticides, although often fairly effective, has been accompanied by other problems. The broadcast application on a field basis may not provide the uniform and concentrated amounts necessary at the particular plant. Air currents may carry these chemicals to neighboring areas, to the potential detriment of local inhabitants. And, to the extent the pesticide does not break down and remains in the soil, it may produce by-products, or residual pesticide which can pose a problem of contamination. As an example of the concern regarding the use of chemical pesticides in the home environment, the Legislature of New York State recently enacted a law mandating that the application of registered pesticidal and herbicidal chemicals to home lawns, by companies that supply such services, must be preceded by a pre-notification to neighboring homeowners, in order to allow them the opportunity to avoid such contact by family members and pets. Thus even registered products, which must meet some level of acceptable safety, are recognized as having inherent toxicological concern. No such warnings are required when such materials are applied to agricultural soils, where population densities are lower, and where the involved parties are generally more attuned to attendant risks of synthetic chemicals.

Most methods currently known to the prior art for producing chitinase enzymes rely upon procedures for genetically modifying plants via the introduction of various genes into plants, microbes and/or a fermentation process based upon use of chitin in its pure form, since various forms of microbes will typically regulate gene expression for adapting to the environment and, thereby, cease chitinase production when other, often more amenable, sources of nitrogen and carbon are available in the environment.

Public resistance to the use of genetically-modified organisms ("GMOs") is increasing, particularly (and not surprisingly!) in countries within the European Union. As a consequence, the public debate regarding the commercialization of GMOs may limit practical marketability and otherwise necessary usage. In developing countries, the costs associated with the need for purified chitin for such fermentation poses a significant problem, in terms of economic viability, of a technology which competes with conventional fertilizer and pesticides. Current pricing of purified chitin can be as high, if not higher, than $(US)20/lb.

The use of raw shrimp shells poses a problem, as well, for the production of chitinase, since their primary use is in the food industry, where fresh shrimp shells contain too high a percentage of water to compete with the commercial chemicals used for fertilizer and pesticide.

The only viable economic source—dried shrimp shell—have two drawbacks which limit their use for such applications:

(1) Dried shrimp shells produce a pungent and unpleasant odor, which makes the direct use of such material, especially for domestic lawn and garden care, impractical from a commercial standpoint.

(2) Dried shrimp shells contain up to 40% protein, some of which are known allergens; a powerful argument against their use for applications outside of fish food for pisciculture. Additionally, proteins delay the onset of chitinase enzyme production by the fermentation microbial community, since the proteins are a more desirable carbon and nitrogen source.

The present invention is, therefore, the result of a search for a natural means for maintaining, controlling, protecting and feeding lawns, turf and home gardens, and thereby replacing chemical pesticides, which are facing increasing disfavor and concern among the general populace. More particularly, the presently claimed invention is concerned with the efficacy of naturally-generated chitinases as biocontrol agents, and whether it is possible to control this powerful natural system as a substitute for the more troublesome chemical pesticides in reducing pathogens in plant growth areas of high contact with humans. The term "turf" as will be used in the present Specification should be understood to include the broad expanses of grasses, such as in golf courses and public parks, where exposure to large numbers of persons is common.

This need, which is met by the present invention, has produced chitinase-related compositions and their methods for use, which unexpectedly combine the desired attributes of natural biocidal activity, herbicidal action, and soil fertilization with low toxicity and allergenicity. The invention derives from the adaptive tendency of certain soil bacteria to generate a class of gycolytic enzymes, particularly chitinases, from flaked or particulated chitin, a naturally-occurring by-product of the seafood industry. It also includes, the fortuitous creation of nitrogenous fertilizing materials resulting from the degradative action of the induced chitinase on the chitin feedstock. These and other aspects of the present invention will become evident in this Specification.

SUMMARY OF THE INVENTION

It is, therefore, an object of the present invention to provide a method for producing and using an induced formation of chitinase in lawn and garden soil for the control of destructive insects and microorganisms, thereby minimizing the need for conventional, artificially manufactured, pesticides.

It is a further object of the present invention is to provide a method for protecting lawns, gardens, and turf through the action of chitinase enzymes to destroy or inhibit soil pathogens, including nematodes, insects and pathogenic fungi.

It is, yet, a further object of the present invention to provide a method for inducing the in situ generation of chitinase enzymes by the action of soil bacteria on chitin introduced into the soil.

An additional object of the present invention is to provide a method for purifying chitin, for soil amendment, to eliminate human allergens.

It is an object to the present invention to also include a partially-degraded chitin with the intact chitin to provide a more-readily available nitrogen source for plant growth.

A further object of the present invention is to provide a bacterial amendment to the soils of home lawns and gardens, and turf, where the bacterial cultures have been pre-optimized with respect to their chitinase-inducing activity.

The foregoing and related objects are achieved by the present invention, which provides chitin-based compositions and related methods for protecting lawns, gardens and turf from pathogens such as nematodes, other insects and fungi, while avoiding the use of chemical pesticides, by inducing the production of chitinase by bacteria in the surrounding soil. The enzyme is induced in the soil bacteria in response to the addition of chitin to the soil. In one instance, for example, the bacteria are those occurring naturally in the soil, and which have the ability to synthesize chitinase enzyme under appropriate stimulation. In another situation, chitin is added to the soil in combination with bacteria which possess enhanced chitinase-producing ability.

In a preferred embodiment of the present invention, the chitin and bacteria amendment also comprises stimulants which favor the chitinase induction by the bacteria in the soil environment. The bacteria with enhanced enzyme production can be selected from those occurring naturally, such as, for example, a *Serratia marcescens* bacterial strain (QMB1466), bacterial strains from the genera *Enterobacter, Trichoderma, Pseudomonas* and *Streptomyces* spp., and/or those that have been genetically modified by being encoded with DNA that favor chitinase production.

In a further, preferred embodiment of the present invention, dried shrimp shells are utilized for the production of an economically-viable non-genetically-modified organism-based chitinase lawn and garden care fermentation broth. A food-grade (commercially available) protease enzyme is used for a hydrolysis of proteins as a way for achieving the elimination of undesirable odors, via a protein hydrolysis lag-time reduction during chitinase fermentation. Additionally, the use of food-grade protease enzyme for the hydrolysis of proteins in the dried shrimp shells achieves an allergen decrease and, particularly, decreases protein fractions of approximately 40 KD, which have been revealed to be the most potent allergen group in crustaceans.

Other objects and features of the present invention will become apparent when considered in combination with the following detail description of the invention, which provides certain preferred embodiments and examples of the present invention. It should, however, be noted that the accompany-detailed description is intended to discuss and explain only certain embodiments of the claimed invention and is not intended as a means for defining the limits and scope of the invention.

DETAILED DESCRIPTION OF THE PREFERRED EMBODIMENTS

The present invention provides compositions and methods for inducing chitinase enzyme production in the soil of lawns, home gardens and turf, to destroy or lessen the effects of soil pathogens on the growing plants, and thereby avoiding the use of synthetic pesticidal chemicals. The term "pathogen" in this context refers to those insect and microbial species which are deemed harmful to growing plants and includes, but is not limited to, beetles, grubs, nematodes, other insects inimical to normal plant growth and fungal species injurious to plants. The term "plants" includes all stages of the growing vegetation, from seed to a fully mature plant. Synthetic pesticidal chemicals refers to those chemical compounds, including herbicides, insecticides, nematocides, larvacides and related materials that are used to treat lawns, home gardens and shrubs to reduce or eliminate unwanted insect and fungal soil organisms.

The induced generation of chitinase in the soil is brought about by the addition thereto of chitin, the presence of which stimulates microorganisms that are present and/or intentionally added, so as to elaborate chitinase enzyme. The chitin can be provided either as a component of naturally occurring materials, such as from seafood wastes, or in some purified form. The addition of chitin to the soil is either by distribution over the surface of a developed lawn, garden or turf, or by direct inclusion into the soils of new growth areas. When distributed over the soil of a developed area, the level of use generally varies from about 100 grams/meter$^2$ to about 500 grams/meter$^2$ of the "as is" material. The form of the chitin can be either powder, prill, granule or flake, or mixtures thereof. The application can be as either the dry product, as an aqueous slurry or via dispersion of the product. The aqueous dispersion can also include a dispersing and/or thickening or suspending agent, in order to promote uniformity. Appropriate dispersing, thickening or suspending agents can be readily determined by those skilled in the art of selecting appropriate materials for uniform delivery of particulated material.

In a preferred embodiment a combination of several physical forms of chitin will allow rapid initial stimulation of microbially-induced chitinase, these forms ranging from finely divided chitin, to coarser forms, with lower surface-to-volume ratios, which result in a protracted delivery of chitin to soil environment. More rapid inducement of chitinase activity occurs when the chitin is incorporated into the soil than when broadcast onto its surface. This results from the low aqueous solubility of chitin. Incorporation into soil allows for a more ready access to it by soil microorganisms than would be the case by its slow leaching from soil and growing surfaces.

In a preferred embodiment, the soil is partially digested by fermentation or chemical means, which deacetylates and/or cleaves the chain of the carbohydrate chitin and increases its aqueous solubility through the production of smaller polymeric units and/or increased availability of polar hydroxyl groups on the glucosyl moieties. Deacetylation, to the degree that it occurs, leaves a primary amino group on the glucosyl unit, which group can serve as a potential source of ammonia, a preferred form of nitrogen for fertilization.

In general, fermentation of chitin can be brought about by adding chitin to a well aerated aqueous slurry in the presence of a small amount of soil from the area to be treated, along with continuous agitation. The reduction of polymer chain length (depolymerization) can be accomplished through the action of aqueous acidic or alkaline agents. Specific details of these operations are well know to those skilled in the art. Preferred degrees of fermentation are in the range of about 10% to about 90%. Preferred degrees of deacetylation are those which reduce the level of nitrogen in the chitin from about 6.9% to the range of approximately 1% to approximately 4%.

In a preferred embodiment of the present invention, the chitin soil amendment can be supplemented with specific bacteria. The bacteria can be, for example: (a) *Lytobacter kobii*, wherein the chitanase and glucanase elaborations of which have been shown to be capable of controlling summer patch disease of Kentucky bluegrass; or (b) directly obtained from the particular lawn, garden or turf to be treated and externally optimized to create chitinase or (c) common bacterial strains which experience has shown can be stimulated to produce chitinase in the presence of chitin. The bacteria do not include those which have been genetically modified to produce chitinase, through insertion of a specific gene which codes for its production. The chitin and bacterial mix can range in composition from about 1000:1 of chitin (as is, dry basis) to bacteria (dry basis, and with 103 cfu/gm population) to about 100:1 by weight.

In a further, preferred embodiment of the invention, the chitin soil amendment can be supplemented with specific nutrients which enhance the proliferation of chitinase-producing bacteria. These nutrients may be included in chitin amendments either with, or without, the addition of specific bacteria, which are naturally predisposed to chitinase production. Such nutrients include, but are not limited to, phosphorus and bio-available trace nutrients.

In yet another preferred embodiment of the present invention, a sample of soil from the potential treatment site is subjected to an aerobic fermentation process in which chitin and appropriate inorganic nutrients are used to stimulate the growth of those native bacteria which can most effectively utilize chitin as a carbon source through stimulation of their chitin-degrading enzyme systems. Specific details of such fermentation can be determined by those qualified and adept, by training, to design such aerobic fermentations, but, in general, the following range of compositions, temperatures and conditions will apply; 200-30° C.; amount of chitin added is a function of dissolved oxygen to reduce ammonia generation; buffers or absorptive polymers optionally added to adjust the pH of the mix, and/or free nitrogen. Subcultures of those enzyme-producing optimized bacteria will be selected for use in future situations where the temperature and soil conditions will favor their inclusion in a chitin/bacterial amendment, without the need for pre-optimization of native bacteria that readily utilize chitin through elaboration of chitanase and related glucanases.

In a further, preferred embodiment of the present invention, dried shrimp shells are utilized for the production of an economically-viable non-genetically-modified organism-based chitinase lawn and garden care fermentation broth. A food-grade (commercially available) protease enzyme is used for a hydrolysis of proteins as a way for achieving the elimination of undesirable odors, via a protein hydrolysis lag-time reduction during chitinase fermentation. Additionally, the use of food-grade protease enzyme for the hydrolysis of proteins in the dried shrimp shells achieves an allergen decrease and, particularly, decreases protein fractions of approximately 40 KD, which have been revealed to be the most potent allergen group in crustaceans.

The present invention is further illustrated by the following Examples. Unless otherwise noted, all parts and percentages in the Examples, as well as in this Specification and the claims are by weight.

Example 1

This Example demonstrates the ability of microbially-induced enzymatically-digested chitin to stimulate the growth of a turf grass, as cf. undigested chitin-treated, and control plots. A two-square meter plot of Fescue grass, maintained by the Farmingdale Horticulture Department of the State University of New York, was subdivided into four one-square meter plots. Treatment occurred in late Summer (early September) when the turf grass is dormant. The ambient daytime temperature during treatment was in the mid- to high-80's (° F.) during the day, dropping to the 60's to low 70's overnight. One plot was maintained as the Control. Two others, diagonally across from each other, received quantities of finely-ground chitin (obtained from Aldrich Chemicals) equivalent to 0.5% and 1.0%, by weight, with respect to dry weight of soil, calculated to a depth of four inches. The comminuted chitin was sprinkled over the surface of the respective plots, and both were watered to facilitate permeation of the powder into the underlying loam. A similar degree of watering was applied to the Control plot, as well as the fourth plot, after the following application.

A previously-prepared Biogard® fermentation mix was applied to the fourth plot, as follows: The fermentation mixture was prepared with 10% chitin in spring water and 1 gm of soil, in a covered 2-liter Erlenmeyer flask [total contents of chitin and soil, per two-liters, was 200 gms and 1 gm of soil, respectively. The mixture was continuously agitated for one month, at ambient temperatures, on a Labline Orbit Shaker at 60 cycles/minute. This mixture serves as a microbial library, for stimulating the growth of naturally-occurring chitinase producing microorganisms in the soil. One liter of the two-liter quantity was uniformly distributed over the one-square meter, fourth plot, followed by watering, as described above. The flask was reconstituted to full volume, by adding appropriate amounts of chitin, water and soil. After two weeks, another one-liter portion of the Biogard ferment was again applied to the fourth plot. As appropriate, the two-meter square subdivided plot was watered bi-weekly to minimize drying, to a degree dependent on natural precipitation. Only two 1-liter applications of the Biogard were made, at the two-week interval.

Results: It could be readily discerned, as the Fall growth of the turf resumed (by mid-October), that the plot that had received the Biogard treatment, was significantly greener than the other, adjoining plots. This greening, which was subsequently observed over an X-week/month period, is attributed to a combination of two factors, the relative contribution of each not being determinable however. The factors are the additional nitrogen available from enzymatic cleavage of the glucosamine side chain on the chitin structure, to fertilize the growth of the turf. The other factor is the destruction of growth-inhibiting pathogens in the soil (e.g., fungi) through action of chitinase enzymes elaborated by the organisms which were stimulated to grow by the presence of chitin in the Biogard ferment. The pathogen destruction is brought about by penetration of structural elements (e.g. hyphae) of soil fungi, and the permeability of the resulting structures to the bi-directional flow of critical elements from and into their cells.

Example 2

This Example demonstrates the induced generation of antifungal microflora in soil by addition of chitin to an aqueous soil dispersion, such induction being noted through a comparison of the microfloral distribution in the initial soil with that of the incubated soil/chitin broth. Specifically, 1.0 gram (dry weight) portions of the soil sediment of the Biogard broth prepared for Example 1, and a comparable fresh soil sample were individually shaken with 5 ml of tap water for a few seconds, then centrifuged to obtain the mother liquors. These were serially diluted to 10-4, plated on Noble agar containing 1% finely-comminuted chitin, and incubated at ambient temperature for 4 days. A visual comparison was then made of the microbial populations in the Biogard soil residue and the control soil.

Results: In comparison with the microflora distribution on the control plates, the microflora derived from the Biogard chitin-digest soil showed a much greater preponderance of *Actinomycetes* spp. This was most evident at the macroscopic levels by very strong geosmine smell in both the fermentation and the soil samples treated with chitin. Control soil did not smell of geosmine at all and the Biogard sample was made from the control soil and chitin. Geosmine is the compound which accounts for the strong earthy smell found right after it rains. It is also characteristic of mushroom prone soil and is referred to as the odor associated "la terre des champignons" in France and is an olifactive clue to the possible presence of mushrooms in areas where the later are harvested. Geosmine is released when actinomycete spores germinate. It is a compound which is specific to this class of microorganism and is unmistakable in its smell.

*Actinomycetes* are indigenous soil microbes that form long complex filaments in networks and produce fruiting bodies or asexual spores similar in microscopic appearance to structures found in fungi. Like fungi, *Actinomycetes* assist in soil clumping and cohesion. They also have a profound effect on soil micro-environments by releasing antimicrobial compounds and adding biomass which plays a significant role in soil structure properties. They are also key in the mineralization process and can degrade a wide variety of chemicals including some pesticides and hydrocarbons. In addition, insects and arthropods containing lesions brought on by chitinase can be opportunistically infected by actinomycete spores. The control sample flora were a rich variety of diverse fungal and bacterial colonies. This demonstrates that the addition of chitin to moist soil stimulates the growth of those organisms which can readily metabolize this substrate, through the elaboration of the chitinase enzymes necessary for its utilization as a food source. Such organisms, e.g. the *Actinomycetes* spp. noted here, are recognized antifungal species, by virtue of the chitinase activity associated with fungal destruction.

Example 3

This Example demonstrates the insecticidal properties of an chitinase-elaborated microbial broth, derived from an aqueous soil dispersion containing comminuted chitin. Specifically, the Biogard ferment utilized in Examples 1 and 2, was sprayed as fine droplets onto 30 ants (*teramorium caespitum*) placed in a covered 100×15 mm petri dish. A Control batch of 30 ants were similarly sprayed with a fine tap water spray. The ants were randomly selected from an "ant-farm" purchased through the mail from a Toys-R-Us® store, and appeared stressed from shipping. The ants were allowed to remain in the covered dish for 24 hours, under ambient conditions, and were not fed during this period.

Results: After the one-day period, 12 of the 30 Control ants had died, while all 30 of the Test ants had died. This demonstrates that the soil/chitin-digest contained insecticidal materials, undoubtedly chitinase enzyme produced by the soil bacteria in the incubated soil-chitin digest. The chitnase attacks and partially digest the outer cuticle of the ants body, making it porous and susceptible to environmental pathogens, including soil bacteria.

Example 4

This Example demonstrates that an aqueous soil digest, containing suspended chitin, will generate materials that can inhibit the germination of undesired, airborne seeds of a competitive species, which might fall on an established turf or lawn. Specifically duplicate sets of 50 Fescue seeds (genus *Festuca*) were placed on 30 grams of moist soil (20 grams dry weight at 50% water-holding capacity) at the bottom of two-liter Erlenmeyer flasks. To the Test flask was added 0.2 gms, dry-weight basis, of the residue from a Biogard digest equivalent to that described in the preceding Examples. This residue, which represents 1% of the 20-gm of dry weight soil, was distributed uniformly over the soil bed. For the subsequent one-week period, both soils were maintained at a constant water-holding capacity, by periodic weighings and aqueous supplementation as needed.

Results: There was an 100%-germination inhibition of the seeds in the Biogard digest-treated Test flask, whereas there was obvious germination of the seeds in the Control flask. This Example demonstrates that while a soil-chitin digest can stimulate (i.e., fertilize) the growth of an established lawn, it can concomitantly inhibit the germination of potentially-competitive seeds which may have randomly deposited onto the soil bed. The inhibition probably results from the cidal action of digest-containing chitinase on the fungal species associated with the seeds, the involvement of which is a recognized and necessary component of seed germination.

While only several embodiments of the present invention have been shown and described, it will be obvious to those skilled in the art that many modifications may be made to the present invention without departing from the spirit and scope thereof.

What is claimed is:

1. A method for controlling the growth of destructive insects and microorganisms in ground soil, comprising the steps of:
   adding chitin to ground soil for inducing bacteria in the ground soil to synthesize chitinase; and,
   deacetylating carbohydrate chains of the chitin for reducing nitrogen in the chitin from approximately 6.9% to the range of approximately 1% to 4% and for increasing its aqueous solubility by producing smaller polymeric units or by increasing availability of polar hydroxyl groups on glucosyl moieties thereof.

2. The method for controlling the growth of destructive insects and microorganisms in ground soil according to claim 1, wherein said deacetylating step is carried out via fermentation.

3. The method for controlling the growth of destructive insects and microorganisms in ground soil according to claim 2, wherein said fermentation is carried out via a process comprising the steps of:

forming an aerated aqueous slurry comprising a small amount of the ground soil from an area of the ground soil to be treated; and, adding chitin to said aerated aqueous slurry under continuous agitation.

4. The method for controlling the growth of destructive insects and microorganisms in ground soil according to claim 1, further comprising the step of:

adding bacteria to the chitin to form a bacterial mix.

5. The method for controlling the growth of destructive insects and microorganisms in ground soil according to claim 4, wherein said bacteria added to the chitin to form said bacterial mix is *Lytobacter kobii*.

6. The method for controlling the growth of destructive insects and microorganisms in ground soil according to claim 4, further comprising the step of:

adding a nutrient to said bacterial mix for enhancing proliferation of chitinase-producing bacteria.

7. The method for controlling the growth of destructive insects and microorganisms in ground soil according to claim 1, wherein said deacetylating step is carried out via an aerobic fermentation.

8. A method for controlling the growth of destructive insects and microorganisms in ground soil, comprising the steps of:

adding chitin to ground soil for inducing bacteria in the ground soil to synthesize chitinase;

deacetylating carbohydrate chains of the chitin for increasing its aqueous solubility by producing smaller polymeric units or by increasing availability of polar hydroxyl groups on glucosyl moieties thereof; and, adding *Lytobacter kobii* to the chitin to form a bacterial mix.

9. The method for controlling the growth of destructive insects and microorganisms in ground soil according to claim 8, wherein said deacetylating step is carried out via fermentation.

10. The method for controlling the growth of destructive insects and microorganisms in ground soil according to claim 8, wherein said fermentation is carried out via a process comprising the steps of:

forming an aerated aqueous slurry comprising a small amount of the ground soil from an area of the ground soil to be treated; and, adding chitin to said aerated aqueous slurry under continuous agitation.

11. The method for controlling the growth of destructive insects and microorganisms in ground soil according to claim 8, wherein said deacetylating step is carried out to reduce nitrogen in the chitin from approximately 6.9% to the range of approximately 1% to 4%.

12. The method for controlling the growth of destructive insects and microorganisms in ground soil according to claim 8, further comprising the step of:

adding a nutrient to said bacterial mix for enhancing proliferation of chitinase-producing bacteria.

13. The method for controlling the growth of destructive insects and microorganisms in ground soil according to claim 8, wherein said deacetylating step is carried out via an aerobic fermentation.

\* \* \* \* \*